United States Patent
Brady et al.

(10) Patent No.: US 9,151,152 B2
(45) Date of Patent: Oct. 6, 2015

(54) THERMAL OPTICAL FLUID COMPOSITION DETECTION

(75) Inventors: Dominic Brady, Winchester (GB); Arthur H. Hartog, Martyr Worthy (GB)

(73) Assignee: Schlumberger Technology Corporation, Sugar Land, TX (US)

(*) Notice: Subject to any disclaimer, the term of this patent is extended or adjusted under 35 U.S.C. 154(b) by 379 days.

(21) Appl. No.: 13/528,395

(22) Filed: Jun. 20, 2012

(65) Prior Publication Data
US 2013/0341008 A1    Dec. 26, 2013

(51) Int. Cl.
*E21B 47/00* (2012.01)
*E21B 47/10* (2012.01)
*E21B 47/06* (2012.01)
*G01N 33/28* (2006.01)

(52) U.S. Cl.
CPC ........... *E21B 47/1005* (2013.01); *E21B 47/065* (2013.01); *G01N 33/28* (2013.01)

(58) Field of Classification Search
CPC ..... E21B 47/00; E21B 47/065; E21B 47/102; E21B 47/1005; E21B 2049/085; E21B 36/04; E21B 49/08; G01N 33/28; G01N 2021/3125; G01N 2021/6484; G01N 2021/656; G01J 3/02; G01J 3/0286; G01J 3/0291; G01J 3/10; G01J 3/42; G01J 1/04; G01J 1/0425; G01J 5/00
USPC .................. 374/136, 130–132, 161; 340/104; 166/66, 250.03, 250.01, 64, 264
See application file for complete search history.

(56) References Cited

U.S. PATENT DOCUMENTS

| | | | |
|---|---|---|---|
| 4,206,638 A | 6/1980 | Djorup | |
| 4,418,568 A | 12/1983 | Surman | |
| 4,435,978 A | 3/1984 | Glatz | |
| 4,604,902 A | 8/1986 | Sabin et al. | |
| 4,770,037 A | 9/1988 | Noir et al. | |
| 4,787,251 A | 11/1988 | Kolodjski | |
| 5,115,127 A | 5/1992 | Bobb et al. | |
| 5,208,650 A | 5/1993 | Giallorenzi | |
| 5,226,333 A | 7/1993 | Hess | |
| 5,551,287 A | 9/1996 | Maute et al. | |
| 5,582,064 A | 12/1996 | Kluth | |
| 5,754,293 A | 5/1998 | Farhadiroushan | |
| 5,991,026 A | 11/1999 | Kluth et al. | |

(Continued)

FOREIGN PATENT DOCUMENTS

GB    2126820 A    3/1984
WO    9945235 A1    9/1999

OTHER PUBLICATIONS

Bruun, H.H., "Hot-wire Anemometry Principles and Signal Analysis", Oxford University Press, New York, 1995, pp. 343-351.

(Continued)

*Primary Examiner* — Jennifer H Gay
*Assistant Examiner* — Steven MacDonald
(74) *Attorney, Agent, or Firm* — David J. Groesbeck

(57) ABSTRACT

A fiber optic sensing tool assembly is deployed in a wellbore that penetrates a hydrocarbon-bearing formation of interest to measure fluid composition and other fluid characteristics. This measurement is implemented by deploying the tool in a region in which there is substantially no fluid flow and by heating the tool through an optical delivery system. Parameters of the fluid are monitored as a function of the heating of the tool to derive information that is indicative of fluid composition and other fluid characteristics.

24 Claims, 5 Drawing Sheets

(56) References Cited

U.S. PATENT DOCUMENTS

| | | |
|---|---|---|
| 6,497,279 B1 | 12/2002 | Williams et al. |
| 6,671,057 B2 | 12/2003 | Orban |
| 6,681,624 B2 | 1/2004 | Furuki et al. |
| 6,946,645 B2 | 9/2005 | Tarvin et al. |
| 7,832,276 B2 | 11/2010 | Wu et al. |
| 7,946,341 B2 | 5/2011 | Hartog et al. |
| 8,074,713 B2 | 12/2011 | Ramos et al. |
| 2004/0252748 A1* | 12/2004 | Gleitman ............... 374/130 |
| 2006/0214098 A1 | 9/2006 | Ramos |
| 2008/0083273 A1* | 4/2008 | Sroka et al. ............. 73/152.55 |
| 2009/0199630 A1 | 8/2009 | DiFoggio et al. |
| 2011/0249266 A1 | 10/2011 | Kumar |
| 2011/0284219 A1 | 11/2011 | Pomerantz et al. |
| 2012/0132417 A1 | 5/2012 | Dria et al. |

OTHER PUBLICATIONS

Kashyap, Raman, "Chapter 4: Theory of Fiber Bragg Gratings", Fiber Bragg Gratings, Academic Press, Second Edition, Sand Diego, 1999, pp. 119-187.

* cited by examiner

THERMAL OPTICAL FLUID COMPOSITION DETECTION

BACKGROUND

Hydrocarbon fluids, such as oil and natural gas, are obtained from a subterranean geologic formation, referred to as a reservoir, by drilling a well that penetrates the hydrocarbon-bearing formation. Once a wellbore is drilled, various well completion components may be installed to control and enhance the efficiency of producing the various fluids from the reservoir. In some oilfields, the fluid produced from the well may include a high concentration (e.g., up to 10%) of sour gas (e.g., hydrogen sulfide). This sour gas, together with the majority of the lighter fractions of the produced hydrocarbon fluids, may be re-injected into the reservoir either as a means of disposal or to enhance production of the base hydrocarbon fluid. However, injection cycling can cause changes in the composition of the hydrocarbon fluid being produced through the wellbore. These fluid composition characteristics may be measured during well intervention procedures during which production is temporarily stopped and appropriate sensors can then be deployed in the wellbore. In sour fields, however, the presence of the sour gas can either impede or altogether prevent the opportunity to perform these types of measurements during an intervention operation.

BRIEF DESCRIPTION OF THE DRAWINGS

Certain embodiments are described with reference to the accompanying drawings, wherein like reference numerals denote like elements. It should be understood, however, that the accompanying drawings illustrate the various implementations described herein and are not meant to limit the scope of various technologies described herein. The drawings show and describe various embodiments.

DETAILED DESCRIPTION

Figure 1:
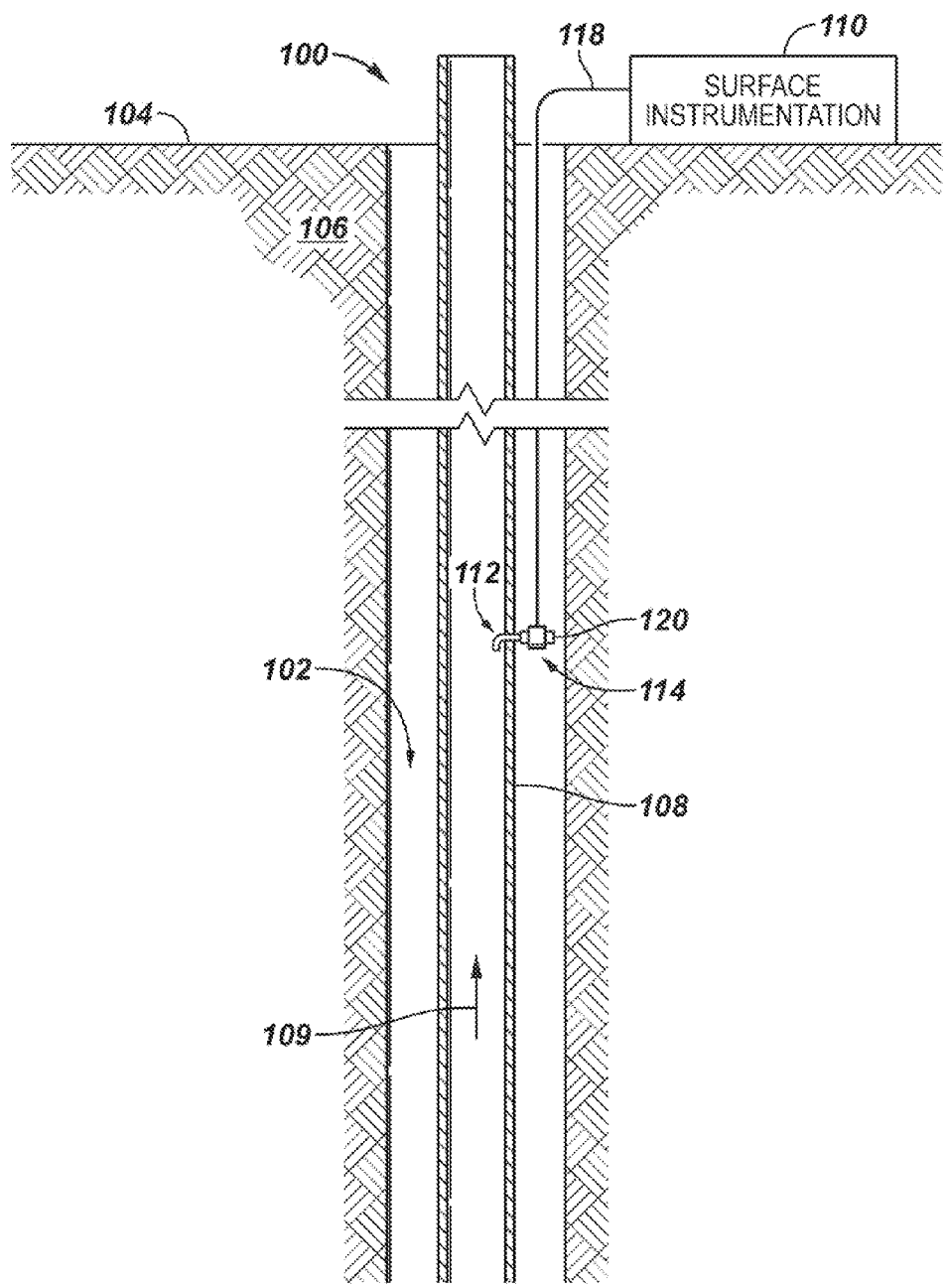
FIG. 1 is a schematic illustration of a fiber optic fluid composition sensor tool deployed in a wellbore, according to an embodiment.

In the following description, numerous details are set forth to provide an understanding of the apparatus and techniques described herein. However, it will be understood by those skilled in the art that these apparatus and techniques may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments.

Available techniques and sensing tools that can be used to determine the composition of a wellbore hydrocarbon fluid are not particularly well-suited for sour oilfield applications where produced hydrogen sulfide and other gases are re-injected into the reservoir. The hazardous environment present in such applications provides limited opportunity for deploying or replacing sensing tools in the wellbore, such as during intervention operations. Thus, these applications demand the use of high reliability sensing tools that can withstand the acidic environment for extended periods of time. Consequently, conventional electronic sensor systems generally are not suitable.

Accordingly, various embodiments comprise methods and apparatus that include sensors that can be permanently installed in the wellbore to provide measurements from which the composition of the wellbore fluid can be determined. The methods and apparatus employ fiber optic sensor tools and measurement techniques to measure parameters indicative of fluid composition in the wellbore and, thus, are able to withstand the harsh and acidic conditions present in this environment. The use of fiber optic sensors enables the deployment of a sensor installation where the electronic interrogation and acquisition system can be located remotely from the well, thus overcoming the obstacles presented when working in the hazardous conditions in a sour field. In addition, a fiber optic measurement system generally has a large bandwidth, which facilitates multiplexing of data obtained by the sensors over substantial distances without being overwhelmed by noise generated by electromagnetic interference. Yet further, because there are no electronic components installed downhole, a fiber optic measurement system provides for increased durability, reliability and longevity.

In general, in various embodiments, a fiber optic sensing tool assembly is deployed in a wellbore that penetrates a hydrocarbon-bearing formation of interest to measure fluid composition and other fluid characteristics. This measurement is implemented by deploying the tool in a region in which there is no appreciable fluid flow (e.g., in a closed off well stub, for instance, where the fluid may circulate slowly relative to the timescale of any measurement) and by heating the tool through an optical delivery system. Parameters of the fluid are monitored as a function of the heating of the tool to derive information that is indicative of fluid composition and other fluid characteristics.

Turning now to FIG. 1, a fiber optic measurement system 100 for determining a characteristic of a hydrocarbon fluid present in a production wellbore 102 that extends from the earth surface 104 into a formation of interest 106 is schematically illustrated. In this embodiment of FIG. 1, the characteristic determined by the system 100 is composition of the wellbore fluid. As shown in FIG. 1, a production tubing 108 has been deployed in the wellbore 102 for delivering the hydrocarbon fluid 109 from the formation to the surface 104. A closed off stub 120 is fluidly coupled to the tubing 108 by a fluid pathway 112 such that the hydrocarbon fluid 109 also is present in the stub 120 but does not have an appreciable flow rate. A fiber optic sensor tool 114 is deployed in the wellbore 102 to monitor one or more parameters indicative of the fluid composition of the fluid within the stub 120, and thus, the fluid 109 within the production tubing 108.

The fiber optic sensor tool 114 is coupled to a surface instrumentation system 110 via a length of optical fiber cable 118. In some embodiments, the cable 118 may be deployed in the wellbore through a tubing or control line that is present in the annulus formed between the production tubing 108 and the wall or casing of the wellbore 102. The surface instrumentation system 110 may be located in the vicinity of the wellbore 102 or may be located at a substantial distance from the wellbore 102. In general, the surface instrumentation system 110 includes optical interrogation and acquisition components configured to obtain information from the sensor tool 114 that is indicative of various parameters of interest from which characteristics (e.g., fluid composition) of the well fluid can be ascertained, in accordance with the techniques and principles described herein.

Figure 2:
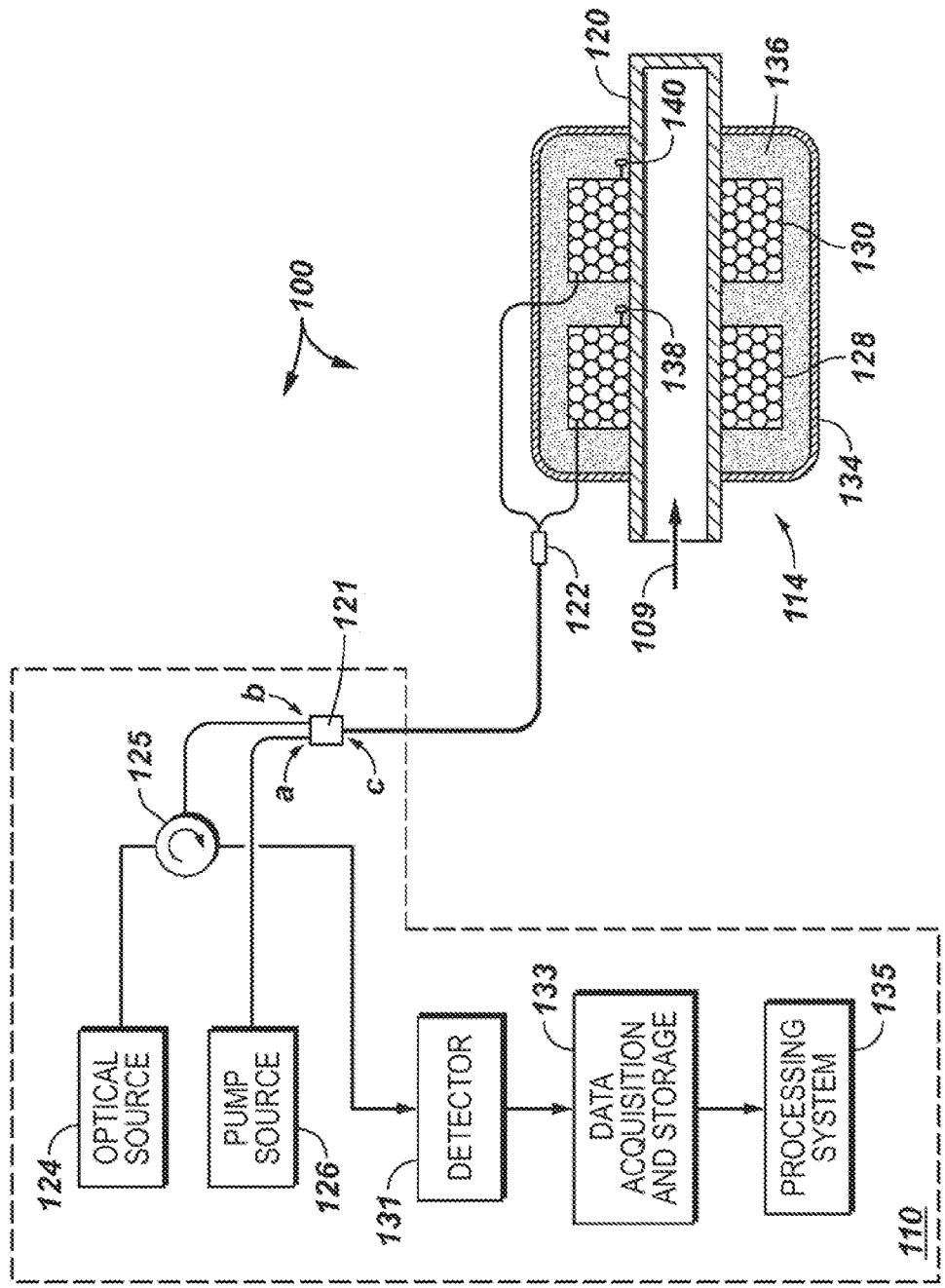
FIG. 2 is a schematic illustration of a fiber optic fluid composition measuring system including a physical representation of a fiber optic sensing tool, according to an embodiment.

Turning now to FIG. 2, an embodiment of the fiber optic sensor system 100 is schematically illustrated. System 100 is configured as an optical fiber interferometer (e.g., a Michelson fiber interferometer) having optics contained within the tool 114 deployed downhole in the wellbore 102. The tool 114 includes an optical coupler 122 that directs optical signals generated by optical sources 124 and 126 in the surface system 110 to two fiber optic sensing elements 128 and 130 of the tool 114. Elements 128 and 130 act as the arms of the interferometer. Both fiber optic elements or arms 128 and 130 are thermally coupled to the fluid in the stub 120. Arm 128 is configured as a heater element that converts optical energy to thermal energy that is then coupled to the well fluid. Arm 130 is a reference element that, in conjunction with the arm 128, measures a parameter of the well fluid (e.g., temperature).

As mentioned, the surface instrumentation system 110 generally includes components for interrogating the downhole optical tool 114 and acquiring information therefrom. Towards that end, the system 110 includes the optical interrogating source 124 (e.g., a laser) for interrogating the tool 114 by generating an optical signal at a particular optical wavelength. The system 110 also includes the optical pump source 126 (e.g., a laser) for generating an optical signal at a particular wavelength that is used to generate thermal energy in the downhole tool 114. In the embodiment of FIG. 2, the wavelength of the pump optical signal is different than the wavelength of the interrogating optical signal and its light is coupled into a downlead 127 using a wavelength-selective, or wavelength-division-multiplexing (WDM), coupler 121. Coupler 121 transfers the optical signal from the pump source 126 arriving at port "a" into the downlead 127, which is connected to the port "c" of the coupler 121. Port "b" of the coupler 121 is connected to an optical circulator 125 so that the coupler 121 transfers the interrogating optical signal from interrogating source 124 to the downlead 127 via its port "c".

The downhole coupler 122 directs the optical signals generated by the sources 124 and 126 to the two optical arms 128, 130 of the tool 114. To optimize the measurements made by the tool 114, the coupler 122 can be configured to direct the pump optical signal to the heater arm 128 and to split the interrogation pump signal equally between the heater arm 128 and the reference arm 130. However, in other embodiments, a portion of the pump signal can also be directed to the arm 130 and a non-equal split of the interrogation signal between the arms 128 and 130 can be employed.

The downhole coupler 122 also directs optical signals generated by the arms 128 and 130 in response to the interrogating signal to an optical detector 131 in the surface system 110 via the downlead 127 and the circulator 125. The detector 131 converts the received optical signals to electrical signals and provides the electrical signals to a data acquisition system 133. The data acquisition system 133 can store data representative of the electrical signals for later processing and analysis and/or provide the data to a processing system 135 to determine the composition of the fluid in the stub 120.

In FIG. 2, the reference arm 130 includes a coil of undoped optical fiber. The heater arm 128 includes a coil of optical fiber that is doped with an ion that has absorption bands at the pump wavelength of the optical pump source 126 in the interrogation system 110, while also substantially transmissive at the interrogation wavelength of the optical signal generated by the optical interrogation source 124. The stub 120 provides a tool body to which the optical fibers of arms 128, 130 are mounted and thermally coupled to the fluid in the stub 120. In the embodiment of FIG. 2, the stub or tool body 120 is a tube forming a passageway that contains a quasi- or substantially static volume of the hydrocarbon fluid 109 from the production tubing 108. The fluid 109 in the stub 120 is quasi- or substantially static in that there is minimal or no flow through the stub 120. However, as a result of processes, such as diffusion, the composition of the fluid 109 in the stub 120 is representative of the composition of the fluid that is flowing in the production tubing 108. The optical fibers of arms 128 and 130 are coiled about the outer surface of the tube 120. The tube 120 is made of a thermally conductive material to provide the thermal coupling between the arms 128, 130 and the well fluid in the tube 120. The thermally conductive material may be any of a variety of materials that are suitable for the particular environment in which the tool 114 is deployed. For instance, the tube 120 can be made of a corrosion-resistant alloy material, a precious metal (e.g., gold), or a multi-layer material having a corrosion-resistant outer layer over a layer of material that is highly thermally conductive, such as diamond, vitreous carbon, etc. The, thermal coupling provides for transfer of thermal energy from the heater arm 128 to the fluid and allows the temperature of the fluid to be detected by the arms 128 and 130. In this manner, when the arms 128 and 130 are interrogated by an interrogating signal from the surface instrumentation 110 by well-known interferometric techniques, a path imbalance between the arms 128 and 130 may be determined. This imbalance is indicative of the change of temperature of the well fluid within the tube 120 as a function of the amount of pump power delivered to the heater arm 128. More specifically, the imbalance is indicative of the differential temperature between the arms 128 and 130 in response to the heating of the arm 128 that results from the pump power that is delivered to the tool 114 from the pump source 126.

In the embodiment shown, both arms 128 and 130 are physically protected from the fluid in the tube 120 in a manner that shields the optical fibers from effects caused by fluid contact. This protective arrangement increases the longevity of the downhole sensor tool 114. In this example, the arms 128 and 130 are protected within a common enclosure 134 that contains a thermally insulative material 136 (e.g., mineral wools, ceramics, or polymers) that insulates the arms 128 and 130 from one another. By placing both arms 128 and 130 within the common enclosure 134, the arms 128 and 130 experience common mode physical influences (e.g., pressure fluctuations with the fluid) in a similar manner. Consequently, these common mode influences are rejected by the measurement system 100 because the influences act substantially equally on both arms 128 and 130.

Each arm 128 and 130 in FIG. 2 also includes a reflector 138 and 140 (e.g., a mirror), respectively, such that the length of each arm 128 and 130 is generally similar, although differences in length may exist to allow for simple interrogation techniques. In some embodiments, the reflectors 138 and 140 may terminate the optical fibers of the arms 128 and 130. In other embodiments, the tool 114 may include further fiber optic sensing elements. In either event, the reflectors 138 and 140 serve to delimit the location of the corresponding arm 128, 130.

As previously discussed, the optical fibers of the arms 128 and 130 are coiled about the stub or tube 120 to provide a thermal path between the arms 128, 130 and the well fluid within the tube 120. This thermal path transfers the thermal energy generated in the heater arm 128 to the fluid and conveys temperature information from the fluid to the arms 128, 130 in a known manner. For instance, the arms 128 and 130 may be mounted to the tube 120 so that the thermal paths between each arm 128, 130 and the fluid are the same or substantially similar.

In operation, to obtain measurements that are indicative of fluid composition, the pump source 126 in the surface instrumentation 110 generates a pump signal at an appropriate wavelength for absorption by the dopant in the optical fiber of the heater arm 128. The absorption of the pump light transforms the optical energy into thermal energy that is then transferred to the fluid in the tube 132 via the thermal path between the arm 128 and the fluid. The reference (or static) arm 130 acts as a reference to account for common effects of the fluid. Temperature changes of the fluid in the tube 132 can be measured by interrogating the downhole tool 114 using an optical signal at the interrogation wavelength and acquiring returned optical signals that are indicative of the imbalance between the arms 128 and 130.

In some embodiments of the system of FIG. 2, the pump optical source 126 can be pulsed so that the heater arm 128 experiences heating and cooling cycles, which, in turn, result in heating and cooling of the fluid in the tube 120 in the proximity of the heater arm 128. The dynamic effects of heating and cooling cycles induced by pulsing or otherwise modulating the pump optical source 126 can be directly linked to two thermal paths. The first thermal path is the static (structural) path as defined by the physical structure of the sensing tool 114 which causes thermal energy to be lost to the physical components of the sensing tool 114. This path does not contribute to the sensitivity of the sensing tool 114. The second thermal path is the path whereby thermal energy is lost to or from the well fluid in the tube 132 due to the heating/cooling cycles. The energy in this thermal path is a function of the duration of the heating/cooling pump cycles and the path thermal conductivity, density and heat capacity of the well fluid. The surface system 110 thus is configured to acquire information from the sensing tool 114 as a function of the pump signal generated by the pump optical source. In this manner, the sensing tool 114 provides measurements of the temperature difference between heated and not-heated states that are indicative of the thermal conductivity, density and heat capacity of the well fluid. These measurements, when combined with other measurements (such as temperature, pressure and density) in the vicinity of the sensing tool 114 and a priori knowledge of the characteristics of the produced and injected fluid, allows for determination of the composition of the well fluid that is present within the stub 120 (and, consequently, in the production tubing 108). When pulsing source 126, the time-dependence of the interferometer response from the tool 114 and/or the peak change in the interferometer output detected by the system 110 can be used to infer the composition of the well fluid 109.

A fiber optic sensing system that employs interferometry principles generally produces measurements that are highly sensitive to temperature changes. In other embodiments, interferometer configurations other than the configuration shown in FIG. 2 can be implemented. In addition, sensing methods other than interferometry can be used to detect the temperature changes of the fluid in the stub 120. As an example, temperature changes could be measured using any of a variety of optical sensing techniques, such as fiber Bragg gratings, or distributed temperature sensors based on Raman, Brillouin or coherent Rayleigh backscatter methods that may function with or without reflective features within the sensing fiber to mark the start/end of the heating and reference sections of fiber. Examples of suitable distributed temperature sensors are disclosed in International Publication No. WO 2011/162868.

As previously mentioned, the heater arm 128 of the interferometer configuration shown in FIG. 2 includes a doped optical fiber. In one example, the optical fiber of the arm 128 can be doped with $Er^{3+}$ (i.e., erbium), so that a pump wavelength at either 980 nanometers (nm) or 1480 nm and an interrogation wavelength of 1310 nm could be used. An interrogation wavelength of 1310 nm avoids the strong fluorescence from the erbium-doped fiber of the heater arm 128 in the 1450-1650 nm region as a result of the optical pumping. A system configured in this manner could operate over substantial distances (e.g., multiple kilometers) between the surface instrumentation 110 and the downhole sensing tool 114.

In other embodiments, the optical fiber of the heater arm 128 can be doped with different ions. For instance, there are a number of ions that have characteristic absorption and emission wavelengths, cross-sections, and achievable doping levels. These ions include rare-earth ions, such as $Yb^{3+}$, $Pr^{3+}$, $Nd^{3+}$, and $Tm^{3+}$. Transition metals also could be used. These metals exhibit substantially stronger and broader absorption features, with negligible emission, which may be more appropriate in some applications. In some embodiments, particular doping concentrations and/or particular absorption features provided by particular ions may be selected to control the locality of the heating as may be desired for a particular optical or mechanical configuration.

In yet other embodiments, other types of loss mechanisms can be used to convert optical power to thermal energy. For instance, absorption of optical power by O—H or O—D bonds or molecular hydrogen could be employed to generate thermal energy. As another example, gratings can be introduced along the optical fiber of the downhole tool 114. These gratings can be configured to couple light from the core of the optical fiber to unguided modes of the fiber. The deflected light thus would be absorbed in the coating of the optical fiber or in the mechanical protection surrounding the fiber and thereby converted to thermal energy. The use of gratings can be particularly attractive in applications in which there are multiple sensors multiplexed along the length of a single fiber. By configuring the gratings to each deflect at slightly different wavelengths, and by adjusting the wavelength of the pump signal accordingly, each sensor can be interrogated in turn, thus allowing sufficient optical energy to be transferred to each sensor in turn and a sufficiently strong signal in response.

In yet other embodiments, the sensing system 100 may include additional downhole couplers so that one or more optical fibers can be dedicated to conveying the optical pump power to the sensing tool 114 and separate optical fibers dedicated to conveying the interrogation signal to the sensing tool 114. This configuration allows a higher pump power to be carried in the pump fiber than otherwise would be possible in the interrogating fiber. In addition, by using separate fibers to convey the pump and interrogating signals, the fluorescence resulting from absorption of the pump energy by the heater arm 128 will not overwhelm the interrogating optical signal. In such an embodiment, the pump fiber can be a multimode fiber, which allows for substantial increases in optical power in the pump signal before running into power limits that are dictated by the onset of non-linear optical effects.

As also discussed above, in various embodiments, the pump power is pulsed, thus providing for heating and cooling cycles of the fluid in the stub 120. The duration of the heating and cooling cycles has an effect on the timescales of the thermal inertia of the well system in which measurements are being taken. Shorter timescales can be used to probe spatially nearer effects which can provide for optimization of the response of the system to balance noise caused by longer-term system drifts (i.e., 100 mHz and lower frequencies) against the depth, and therefore volume of fluid, probed by the heat pulse. In addition, at the short timescale end of the spectrum (i.e., Hz to tens of Hertz), this effect allows for calibration of the response of the measurement system, while deployed, against the issues caused by the change in the thermal path between the optical fiber sensing elements 128, 130 of the tool 114 and the well fluid as the system ages or due to scale deposits that build up in the thermal path between the sensing elements and the fluid.

As described thus far, the fluid composition sensing system 100 includes a single tool 114 configured as an interferometer with a single heated section 128 acting on a single volume of quasi-static well fluid within the stub 120. However, this specific configuration should not be considered limiting and other embodiments may include more or different types of sensors to obtain more accurate measurements within a single volume or may include more or different types of sensors to obtain measurements within additional volumes of well fluid.

Figure 3:
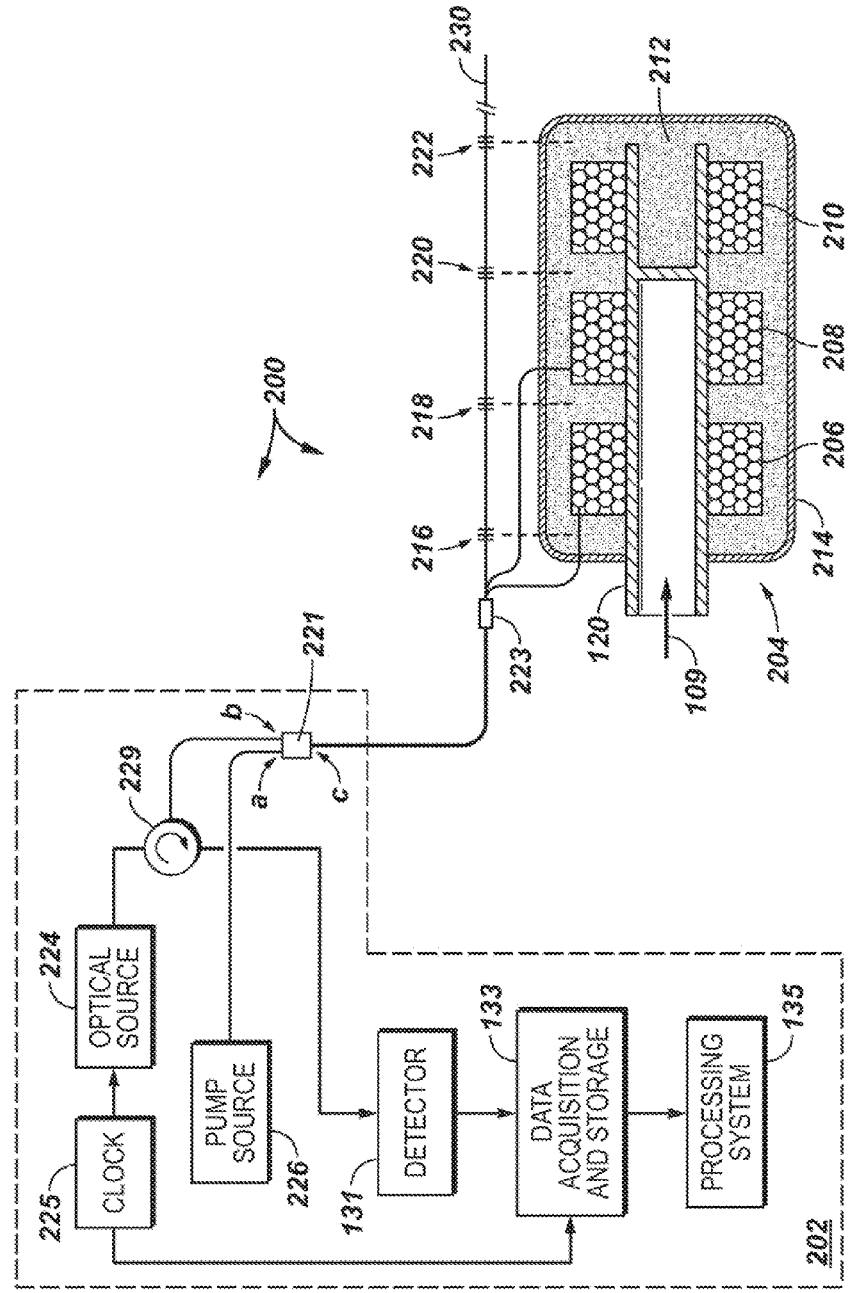
FIG. 3 is a schematic illustration of another fiber optic fluid composition measuring system including a physical representation of another fiber optic sensing tool, according to an embodiment.

For instance, in the embodiment shown in FIG. 3, an interferometer sensing system 200 is used in conjunction with time domain multiplexing techniques implemented by surface instrumentation system 202. In this embodiment, a sensor tool 204 includes three sensing elements 206, 208, 210 mounted on a tool body 212 (e.g., a heat conductive tube or closed off stub). Two of the sensing elements 206 and 208, are thermally coupled to the well fluid 109 present in the stub 120. The third sensing element 210 is not thermally coupled to the well fluid in the stub 120, but instead is thermally isolated from the fluid by the insulative material 212 so that its response to an interrogating optical signal is not affected by temperature changes of the well fluid. The sensing elements 206, 208, 210 are contained within a common enclosure 214 to provide for common mode rejection of common mode external effects (e.g., pressure) and separated from one another by the thermally insulative material 212.

In this embodiment, two of the sensing elements are doped with an appropriate ion, and the third sensing element is undoped and used as a reference element. In one example, the optical fiber of the first sensing element 206 is doped with $Er^{3+}$. The optical fiber of the second sensing element coil 208 is doped with a different dopant (e.g., $Pr^{3+}$). The optical fiber of the third reference sensing element 210 is not doped. The elements 206, 208, 210 are delimited in location by reflectors 216, 218, 220, 222. The tool 204 is coupled to the surface instrumentation 202 via a downhole coupler 223.

Surface instrumentation system 202 includes an optical source 224 to generate an interrogation signal at two different wavelengths at a time controlled by a clock signal 225. The interrogation signals are coupled into the downlead through an optical circulator 229 and ports "b" and "c" of a WDM coupler 221. System 202 further includes a pump optical source 226 to generate a heater optical signal at two different wavelengths that are appropriate for absorption by the dopants in the doped sensing elements 206, 208 The heater power from the source 226 is coupled into the downlead 227 via ports "a" and "c" of the WDM coupler 221. The wavelengths of the interrogation signals are selected so that they are not overwhelmed by the fluorescence generated by the absorption of the pump light by the sensing elements 206, 208 and so that they are not absorbed by either sensing element 206 or 208.

The use of the third undoped sensing element 210 provides for calibration of the sensing tool 202, for instance to compensate for changes in the thermal paths of the first and second sensing elements 206 and 208 that may occur over time. Changes in thermal paths can be determined by obtaining measurements from the first and second doped sensing elements 206 and 208 and comparing them to the measurement obtained from the third, reference element 210.

In some embodiments, the use of different dopants for the first and second sensing elements 206, 208 can be avoided by providing either additional downhole couplers to provide separate paths to deliver the pump light separately to the two sensing elements 206, 208 or a different path to deliver the pump light to the sensing elements 206, 208. In the latter case, for instance, the end 230 of the fiber from the sensing tool 202 can be looped back to the surface system 202 and coupled to the pump source 226, which, in this embodiment, generates pump light at a single wavelength. The length of each sensing element 206, 208 can be selected so that the pump light is entirely absorbed in either the first element 206 or the second element 208 based on the direction in which the pump light is propagating.

It should be understood that the time domain multiplexing system used with the tool 202 shown in FIG. 3 also can be employed with the tool 114 shown in FIG. 2 and, more particularly, in applications in which multiple tools 114 of the type shown in FIG. 2 are deployed to measure fluid composition characteristics of multiple volumes of well fluid.

It should also be understood that the tools 114 and 204 shown in FIGS. 2 and 3 can be configured in other manners. For instance, the sensing elements may not be wrapped about a tube in which the well fluid is present, but may instead be mounted on or wound about a solid mandrel or other tool body that has a low heat capacity. The sensing elements on the tool body in such an embodiment can be overcoated with a thin, heat transmissive material to protect the optical fiber from the environment. In this embodiment, when the tool is placed in the well fluid (such as within a closed off stub or non-flowing side tributary), the thermal interaction between the well fluid and the sensing elements occurs at the outer surface of the tool (as opposed to the inner surface in the configurations shown in FIGS. 2 and 3). In yet another embodiment, rather than overcoating the optical fiber of the tool with a protective layer, the tool can be placed within a protective tubing (e.g., platinum tubing) that is configured to resist the well fluid pressure and protect the optical fiber from corrosion, while also thermally coupling the optical fiber to the well fluid. In yet a further embodiment, the sensing elements can be configured in planar optics mounted on a tool body with waveguides implanted, diffused or defined by surface relief. In such an embodiment, the thermal interface is at the outermost surface of the planar device, which could, for example, be made of sapphire.

In the embodiments described thus far, the sensing tool has been deployed in a quasi-static volume of well fluid. However, in other implementations of the devices and techniques described herein, at least one of the sensing elements (i.e., at least a heater element) of the tool can be thermally coupled to flowing well fluid in the production tubing in the wellbore. Here, the rate of heating and cooling of the thermally coupled heater element will be a function of the rate of fluid flow over the heater element, as well as the density, heat capacity and thermal conductivity of the flowing well fluid. However, the density, heat capacity and thermal conductivity of the well fluid can be measured independently by the sensing elements that are maintained out of the flow (e.g., in a closed off stub). Thus, the information obtained from sensing elements that are maintained out of the flow can be used to correct the output of the sensing element that is thermally coupled to the flow to account for the fluid properties in the wellbore. This correction thus can improve the accuracy of the flow measurement.

Figure 4:
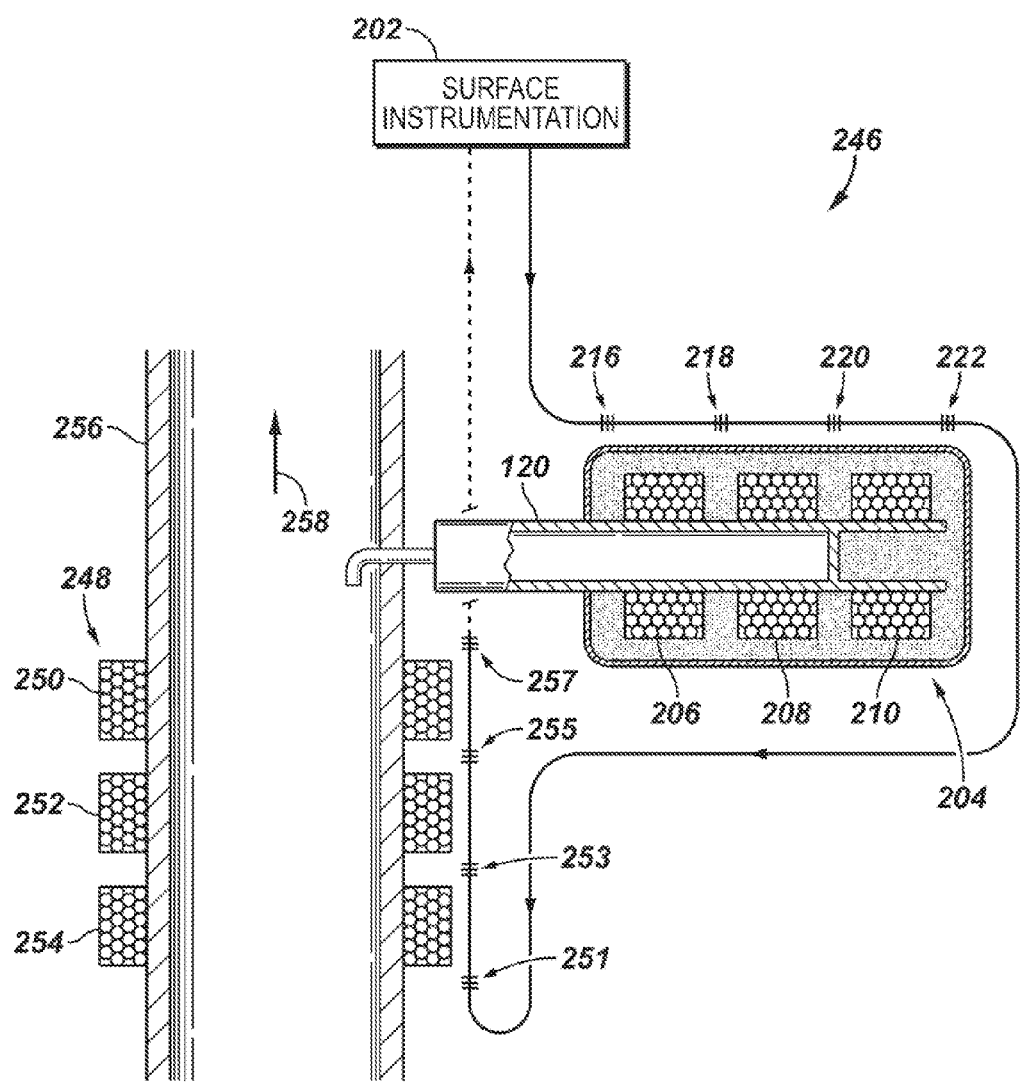
FIG. 4 is a schematic illustration of a fiber optic fluid composition and flow measuring system deployed in a wellbore together with a physical representation of a fiber optic sensing tool, according to an embodiment.

An implementation of a fiber optic measurement system 246 in which additional sensing element(s) are thermally coupled to fluid flow 258 is shown in FIG. 4. In this embodiment, the system 246 includes the surface instrumentation system 202 coupled to the tool 204 to measure parameters of the quasi-static fluid 258 in tube 120 and a second tool 248 to measure parameters of fluid 258 that is flowing in a production tubing 256 in a wellbore. The tool 248 includes fiber optic sensing elements 250, 252, 254 and reflectors 251, 253, 255, 257 that are mounted about the outer periphery of a tool body (here, the production tubing 256), such as by embedding the optical fiber coils in the wall of the tubing 256. In this example, the elements 250, 252, 254 are arranged also to provide information about the direction of the fluid flow. In particular, the central element 252 converts optical energy to thermal energy. Outlying elements 250, 254 are provided on either side of the central element 252 to provide an indication of the direction of the flow. Directional information can be derived by monitoring the temperature of the outlying elements 250, 254 and including time-of-flight to the arrival of the heated fluid at the outlying elements 250, 254. It should be understood, however, that directional information may not be obtained or desired and, thus, that the flow sensing tool 248 may include one of outlying sensing element 250 and 254 adjacent the heating element 252. It should further be understood that directional information can be derived without an actual measurement of time-of-flight since the sensing element that is upstream of the central element will see a smaller heating effect (if any) compared to the sensing element that is downstream of the central element. Thus, the differential sensitivity of the central element 252 between the outlying sensing elements 250, 254 can be sufficient to determine direction of the flow and an estimate of the flow rate.

When directional information is desired (and time-of-flight is included in the measurement), two separate physical phenomena are used. First, the time-of-flight provides a direct estimate of the velocity of the fluid in the vicinity of the tool 248. While there are conduction effects, it is primarily the movement of the fluid that transfers the thermal energy from the heating element 252 to the outlying element(s) 250, 254. A second effect is the temperature rise in the heated region, which is a function of the mass flow of the fluid passing over the heater element 252 and the density, heat capacity and thermal conductivity of the fluid. Thus, by combining the time-of-flight measurement with the temperature rise of the heated region, both the fluid velocity and the thermal properties of the fluid can be determined. Furthermore, when sensing coils 250, 254 are placed on either side of the heating coil 252, the direction of the flow can be ascertained. This configuration also can be used to detect bubbles or heated slugs that pass by the tool 248, thus allowing for detection of other flow characteristics, such as flow regime, in addition to velocity and fluid composition.

While the embodiment of FIG. 4 illustrates the fiber optic elements 250, 252, 254 of the tool 248 wrapped about or embedded in the wall of the production tubing 256, in other implementations, the coils 250, 252, 254 can be mounted on a tool body (e.g., a mandrel) and the tool 248 can be placed directly in the fluid flow in the production tubing 236. In yet other implementations, the tool 248 can be placed directly in a side-flowing tributary off of the main wellbore, where the tributary is of known dimensions and its fluid capture characteristics are understood. By placing the tool 248 in fluid flow in a side tributary, the flow regime can be better controlled and some of the acoustic and mechanical noise that otherwise would be experienced by the tool 248 can be substantially reduced. In addition, placing the tool 248 in a side flow path lends itself to optimization of the thermal coupling between the fiber optic sensing elements 250, 252, 254 and the well fluid due to the reduction in mechanical integrity considerations that otherwise would be an issue if the tool 248 were subjected to the main flow. For instance, in benign environments, the tool 248 can include bare optical fibers. In more chemically aggressive environments, the optical fiber of the tool 248 can be protected by a thin hermetic coating of a noble metal, for instance.

In some well applications, particularly in horizontal or highly deviated wells, the fluid flow can become stratified, with a heavy fluid phase occupying the bottom of the production tubing and the lighter fluid phases occupying the upper portions of the tubing. In these types of applications, a plurality of sensing elements can be placed at various azimuths around the axis of the production tubing to measure the velocity and thermal characteristics of each fluid phase independently.

Figure 5:
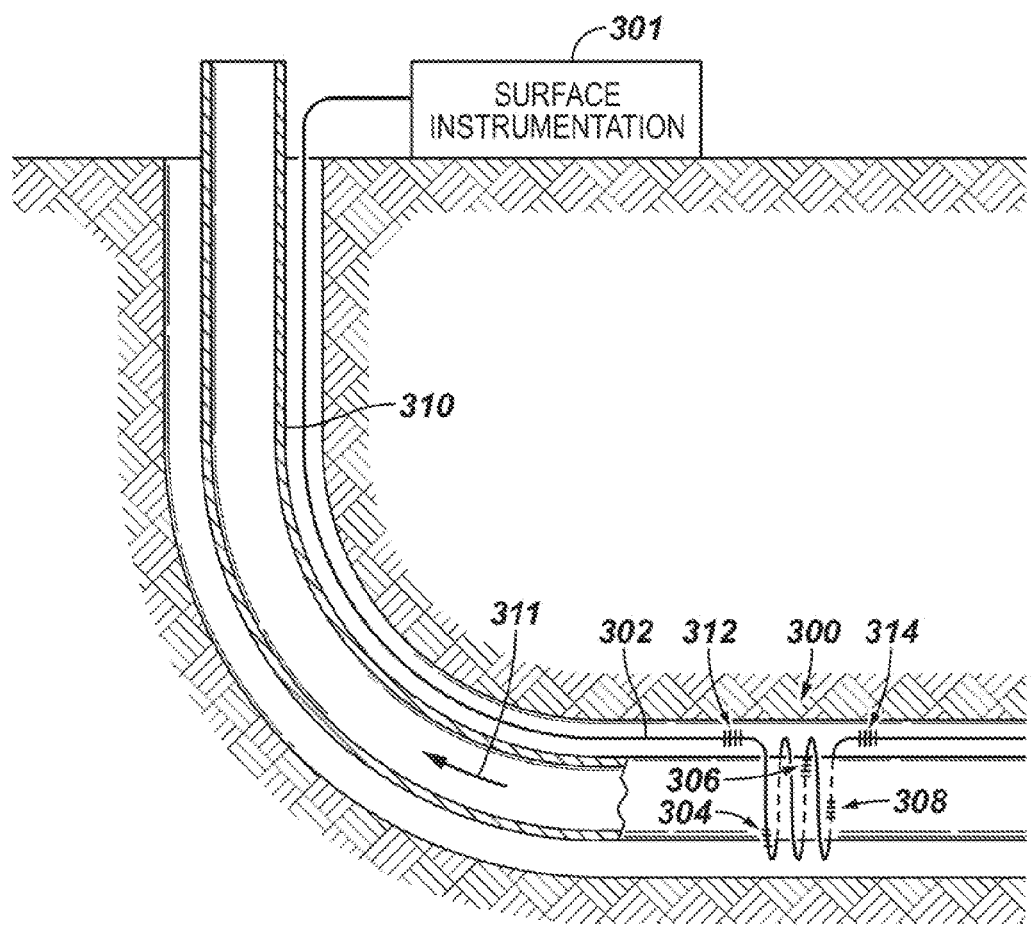
FIG. 5 is a schematic illustration of a fiber optic fluid composition and flow measuring system deployed an a horizontal wellbore, according to an embodiment.

FIG. 5 shows an implementation for achieving azimuth-sensitive sensing of the well fluid. In this embodiment, for ease of illustration, only the fiber optic heating elements (i.e., the blazed fiber Bragg gratings) of a sensing tool 300 are illustrated. As shown, a surface instrumentation system 301 is coupled to an optical fiber 302 with a plurality of blazed fiber Bragg gratings 304, 306, 308 wrapped about a tubing 310 (e.g., production tubing) in which well fluid 311 is flowing. The gratings 304, 306, 308 are arrayed around the outer periphery of the tubing 310 at different azimuths. Each grating 304, 306, 308 is configured to deflect pump power into an absorptive surrounding (not shown) to convert the optical energy into thermal energy. Each grating 304, 306, 308 is configured to deflect optical energy at a different wavelength. Because each grating 304, 306, 308 is located at a different azimuth around the axis of the tubing 310, by varying the wavelength of the pump optical signal, a single interferometer can be used to selectively probe the well fluid in an azimuth-sensitive manner.

In various embodiments, the surface instrumentation 110, 202, 301 can include the processing system 135 (or a portion of system 135) that processes the information acquired from the sensing tools 114, 134, 204, 248, 300 and derives fluid composition, fluid velocity and/or flow direction therefrom using known relationships between the measured parameters and other information (e.g., pressure, temperature, density, a priori knowledge of the composition of the produced fluid and the re-injected fluid). In other embodiments, the processing system 135 may be at a location remote from the wellbore. In other embodiments, the fluid composition, fluid velocity and/ or flow direction may be derived from the measured parameters by an operator or user having access to the measurements obtained by the surface instrumentation system 110, 202, 301.

In some embodiments, the systems and techniques described herein may be employed in conjunction with an intelligent completion system disposed within a well that penetrates a hydrocarbon-bearing earth formation. Portions of the intelligent completion system may be disposed within cased portions of the well, while other portions of the system may be in the uncased, or open hole, portion of the well. The intelligent completion system may comprise one or more of various components or subsystems, which include without limitation: casing, tubing, control lines (electric, fiber optic, or hydraulic), packers (mechanical, sell or chemical), flow control valves, sensors, in flow control devices, hole liners, safety valves, plugs or inline valves, inductive couplers, electric wet connects, hydraulic wet connects, wireless telemetry hubs and modules, and downhole power generating systems. Portions of the systems that are disposed within the well may communicate with systems or sub-systems that are located at the surface. The surface systems or sub-systems in turn may communicate with other surface systems, such as systems that are at locations remote from the well.

It should be understood that embodiments of the tools and methods described herein are not limited to the well structures shown in the illustrative examples. Cased, uncased, open hole, gravel packed, deviated, horizontal, multi-lateral, deep sea or terrestrial surface injection and/or production wells (among others) may incorporate one or more fluid composition sensing tools as described. In many applications, the measurements of the fluid composition may provide useful information that may be used to validate and improve models of reservoir drainage, including geomechanical models that facilitate optimization of the extraction from the reservoir. For example, the tools and methods described herein can serve to detect the breakthrough of injected fluid in more benign conditions, such as in water flood or CO2 injection. In addition, the tools and methods may be employed in applications other than in a hydrocarbon well. For instance, the sensing tools and techniques can be deployed in any structure where fluid composition is of interest. An example application is in flow lines and pipelines where an operator may find it useful to determine if constituents are precipitating out.

While the invention has been disclosed with respect to a limited number of embodiments, those skilled in the art, having the benefit of this disclosure, will appreciate numerous modifications and variations there from. It is intended that the appended claims cover such modifications and variations as fall within the true spirit and scope of the invention.

What is claimed is:

1. A optical fiber sensing tool, comprising:
   a tool body;
   a reference fiber optic element mounted on the tool body and thermally coupled to a substantially static volume of a fluid; and
   a heater fiber optic element mounted on the tool body and thermally coupled to the substantially static volume of the fluid, the heater fiber optic element configured to convert optical energy into thermal energy so that the heater fiber optic element has a temperature that is different than the reference fiber optic element,
   wherein, in response to an interrogating optical signal having an interrogating wavelength, the reference and heater fiber optic elements to provide indications of a temperature change of the substantially static volume of the fluid as a function of the heater fiber optic element converting the optical energy to the thermal energy.

2. The optical fiber sensing tool as recited in claim 1, wherein the heater fiber optic element comprises an optical fiber coiled about the tool body, wherein the optical fiber is doped with an ion that absorbs optical energy at a heater wavelength and substantially transmits optical energy at the interrogating wavelength.

3. The optical fiber sensing tool as recited in claim 2, wherein the reference fiber optic element comprises an optical fiber coiled about the tool body.

4. The optical fiber sensing tool as recited in claim 2, further comprising a fiber optic coupler coupled to the reference and heater fiber optic elements, the fiber optic coupler configured to deliver optical energy at the heater wavelength to the heater fiber optic element and to deliver optical energy at the interrogating wavelength to the reference fiber optic element and the heater fiber optic element.

5. The optical fiber sensing tool as recited in claim 4, wherein the fiber optic coupler splits the optical energy at the interrogating wavelength equally between the reference fiber optic element and the heater fiber optic element.

6. The optical fiber sensing tool as recited in claim 3, wherein the optical fiber of the reference fiber optic element is not doped.

7. The optical fiber sensing tool as recited in claim 3, wherein the tool body comprises a tube containing the substantially static volume of the fluid, and wherein the reference fiber optic element and the heater fiber optic element are coiled about an outer surface of the tube.

8. The optical fiber sensing tool as recited in claim 1, wherein the heater fiber optic element comprises an optical fiber coiled about the tool body, wherein the optical fiber includes a grating to convert optical energy into thermal energy.

9. The optical fiber sensing tool as recited in claim 1, further comprising a further fiber optic element mounted on the tool body and thermally insulated from the substantially static volume of the fluid, the further fiber optic element to provide a reference signal to calibrate the indications of the temperature change provided by the reference and heater fiber optic elements.

10. The optical fiber sensing tool as recited in claim 1, wherein the fluid comprises a hydrocarbon fluid present in a hydrocarbon wellbore, and the tool further comprising:
    a second heater fiber optic element thermally coupled to a flowing portion of the hydrocarbon fluid, the second heater fiber optic element to convert optical energy to thermal energy for transfer to the flowing hydrocarbon fluid;
    a sensing fiber optic element proximate the second heater fiber optic element and thermally coupled to the flowing hydrocarbon fluid, wherein, in response to an interrogating optical signal, the second heater and sensing fiber optic elements provide indications of a characteristic of the flowing hydrocarbon fluid.

11. The optical fiber sensing tool as recited in claim 10, wherein the second heater fiber optic element and the sensing fiber optic element are mounted about an outer periphery of a production tubing in the wellbore in which hydrocarbon fluid is flowing.

12. The optical fiber sensing tool as recited in claim 10, wherein the characteristic is flow rate.

13. The optical fiber sensing tool as recited in claim 11, wherein the second heater fiber optic element and the sensing fiber optic element are mounted about the outer periphery of a horizontal or highly deviated section of the production tubing at different azimuths around the axis of the horizontal section.

14. The optical fiber sensing tool as recited in claim 1, wherein the substantially static volume of fluid is a hydrocarbon fluid located in a hydrocarbon well.

15. A method of measuring fluid composition of a hydrocarbon fluid present in a wellbore, comprising:
  delivering optical energy to a fiber optic sensing tool thermally coupled to a substantially static volume of the hydrocarbon fluid in the wellbore;
  converting, by the fiber optic sensing tool, the optical energy to thermal energy;
  transferring the thermal energy to the substantially static volume of the hydrocarbon fluid; and
  detecting a parameter of the substantially static volume of the hydrocarbon fluid as a function of the delivered optical energy, wherein the detected parameter is indicative of the fluid composition of the hydrocarbon fluid.

16. The method as recited in claim 15, wherein the detected parameter is a change of temperature of the substantially static volume of the hydrocarbon fluid in response to transferring the thermal energy thereto.

17. The method as recited in claim 15, further comprising:
  delivering optical energy to a second fiber optic sensing tool thermally coupled to flow of the hydrocarbon fluid in the wellbore;
  converting, by the second fiber optic sensing tool, the optical energy to thermal energy;
  coupling the thermal energy to the flow of the hydrocarbon fluid; and
  detecting, by the second fiber optic sensing tool, a parameter of the hydrocarbon fluid flowing in the wellbore that receives the coupled thermal energy.

18. The method as recited in claim 17, further comprising correcting the detected parameter of the hydrocarbon fluid flowing in the wellbore based on the detected parameter of the substantially static volume of the hydrocarbon fluid.

19. The method as recited in claim 16, wherein the wellbore is a horizontal or highly deviated wellbore, and the method comprises detecting a parameter of the hydrocarbon fluid flowing in the wellbore with a plurality of fiber optic elements spaced azimuthally around the axis of the wellbore.

20. A fiber optic measurement system for determining fluid composition of a hydrocarbon fluid present in a wellbore, comprising:
  a fiber optic sensing tool deployed in a wellbore to detect a parameter of a volume of substantially static hydrocarbon fluid;
  an optical source to deliver optical energy at a first wavelength to the fiber optic sensing tool, wherein the fiber optic sensing tool converts the delivered optical energy to thermal energy and thermally couples the thermal energy to the volume of substantially static hydrocarbon fluid, the optical source further to deliver optical energy at a second wavelength to the fiber optic sensing tool; and
  a detector to detect a returned optical signal generated by the fiber optic sensing tool in response to the optical energy at the second wavelength, wherein the returned optical signal is indicative of temperature of the volume of the substantially static hydrocarbon fluid as a function of the optical energy delivered at the first wavelength.

21. The fiber optic measurement system as recited in claim 20, wherein the fiber optic sensing tool includes a tool body, a fiber optic heater element mounted on the tool body, and a fiber optic sensor element mounted on the tool body; and wherein the fiber optic heater element converts the optical energy at the first wavelength to thermal energy.

22. The fiber optic measurement system as recited in claim 21, wherein the fiber optic heater element and the fiber optic sensor element are wrapped about the tool body.

23. The fiber optic measurement system as recited in claim 22, further comprising a second fiber optic sensing tool deployed in the wellbore, the second fiber optic sensing tool thermally coupled to a flow of the hydrocarbon fluid in the wellbore.

24. The fiber optic measurement system as recited in claim 23, wherein the wellbore is substantially horizontal, and wherein the second fiber optic sensing tool includes a plurality of fiber optic heater elements spaced azimuthally around the axis of the substantially horizontal wellbore.

\* \* \* \* \*